United States Patent
Venkateswarlu et al.

(10) Patent No.: US 7,385,072 B2
(45) Date of Patent: Jun. 10, 2008

(54) METHODS FOR THE PREPARATION OF ENTACAPONE

(75) Inventors: Jasti Venkateswarlu, Andhra Pradesh (IN); Arava Veera Reddy, Hyderabad (IN); Chinnapillai Rajendiran, Hyderabad (IN); Samjuddin Md Md, Hyderabad (IN)

(73) Assignee: Suven Life Sciences, Banjara Hills, Hyderabad (IN)

( * ) Notice: Subject to any disclaimer, the term of this patent is extended or adjusted under 35 U.S.C. 154(b) by 0 days.

(21) Appl. No.: 11/478,552

(22) Filed: Jun. 29, 2006

(65) Prior Publication Data

US 2007/0060767 A1    Mar. 15, 2007

Related U.S. Application Data

(63) Continuation of application No. PCT/IN03/00401, filed on Dec. 29, 2003.

(51) Int. Cl.
*C07C 255/08* (2006.01)

(52) U.S. Cl. ..................................... 558/401; 564/167

(58) Field of Classification Search ................ 564/167; 558/401

See application file for complete search history.

(56) References Cited

U.S. PATENT DOCUMENTS 4,963,590 A * 10/1990 Backstrom et al. .......... 514/678

OTHER PUBLICATIONS

Wikeberg et al, Drug metabolism and Disposition, vol. 21, No. 1, pp. 81-92, 1993.*

* cited by examiner

*Primary Examiner*—Shailendra Kumar
(74) *Attorney, Agent, or Firm*—Schwegman, Lundberg & Woessner P.A.

(57) ABSTRACT

The invention disclosed in this application relates to an improved process for the preparation of Entacapone. In one embodiment the process involves: (i) reacting a 3-alkoxy-4-hydroxy-5-nitrobenzadehyde with N,N-diethylaminocyanoacetamide in the presence of a mild acid catalyst and a solvent, to provide a 3-O-alkylated Entacapone, and treating the 3-O-alkylated Entacapone with an acid catalyst in the presence of an organic base to provide Entacapone.

19 Claims, No Drawings

METHODS FOR THE PREPARATION OF ENTACAPONE

RELATED APPLICATIONS

This application is a continuation under 35 U.S.C. 111(a) of PCT/IN2003/000401, filed on Dec. 29, 2003 and published on Jul. 14, 2005 as WO 2005/063693 A1, which application is incorporated herein by reference in its entirety and made a part hereof.

BACKGROUND OF THE INVENTION

The preparation of Entacapone, formula (1), has been reported in GB 2,200,109 and U.S. Pat. No. 4,963,590 from two critical intermediates viz; 3,4-dihydroxy-5-nitrobenzadehyde (formula (5)) and N,N-diethylamino-cyanoacetamide (formula (3)). The compound of formula 5 was condensed with compound 3 in the presence of piperidine acetate and dry ethanol as a solvent to provide Entacapone. The 3,4-dihydroxy-5-nitrobenzaldehyde was prepared from 3-methoxy-4-hydroxy-5-nitrobenzaldehyde (6) using acetic acid and hydrobromic acid, as illustrated in Scheme 1.

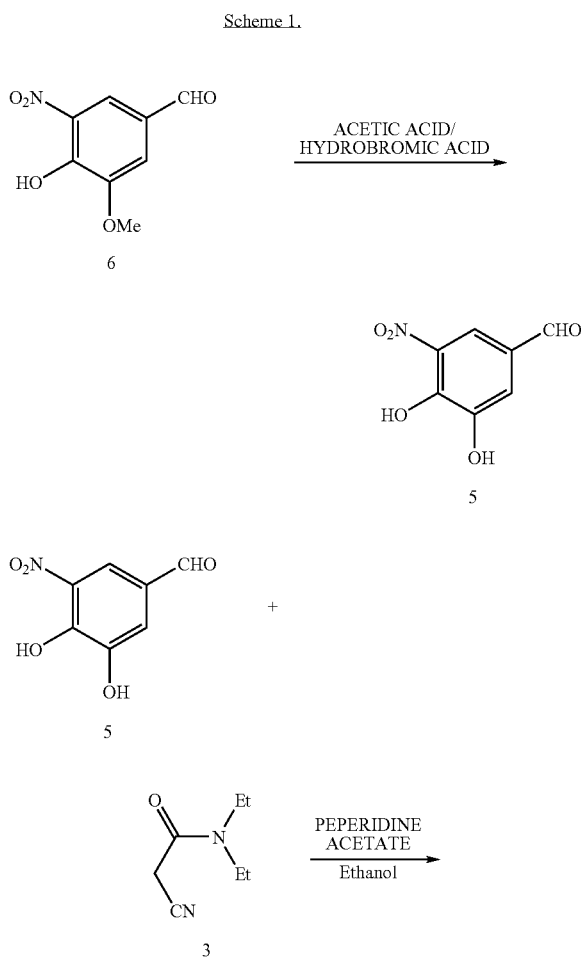

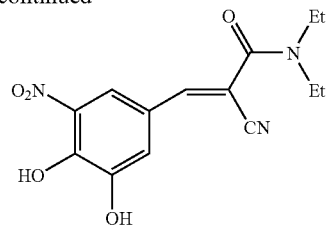

The above patent described the preparation of Entacapone (1) without describing the stereochemistry or the polymorphism.

Subsequently it was described in the U.S. Pat. No. 5,135,950 described preparing the E-isomer and polymorphism-A from the mixture obtained from the reaction reported in the GB Patent No. 2,200,109.

The main disadvantage of this method, according to our findings, is that the reaction times are very long, ranging about 84-100 hours, and the reaction never goes to completion.

Furthermore, the preparation of compound 5 from 3-hydroxy-4-methoxy-5-nitrobenzadehyde 6 as described in Scheme 1 has to be purified repeatedly and the yield compound 5 is only about 55%. Consequently, the yield of the final product is also very low.

The critical raw material 3,4-dihydroxy-5-nitrobenzaldehyde (5), a catechol derivative, changes color from light yellow to a dark color upon storage at room temperature in a short period of time. The yield and quality (purity) of the Entacapone product varies between batches and there is no consistency in yield and quality. Hence storing of this compound required special conditions, such as below 15° C. in the absence of light.

In addition, it was known in the literature that catechol derivatives are known to undergo aerial oxidation and give quinone derivatives. Such oxidations contribute to the color changes during storage.

Accordingly, it is of paramount important to find a stable penultimate stage intermediate that is stable at room temperature for longer durations and can be stored and used required. The overall yield of the Entacapone final product by the present route (described above) is about 58%.

SUMMARY OF THE INVENTION

The present invention relates to an improved process for the preparation of Entacapone. Entacapone having the formula 1 is a potent and specific peripheral catechol-O-methyltransferase (COMT) inhibitor. It can be used in combination with levodopa/carbidopa to treat Parkinson's disease, sometime referred to as shaking palsy. Entacapone can enhance the effect of levedopa/carbidopa by improving muscle control.

The invention also relates to a novel intermediate of the formula 4 where R is ethyl and a process for its preparation.

Accordingly, the invention provides a method for preparing a compound of formula I:

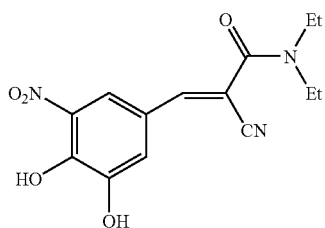

(I)

comprising:

(i) contacting a 3-alkoxy-4-hydroxy-5-nitrobenzadehyde where the alkyl group of the alkoxy is a methyl or an ethyl group, with N,N-diethylamino-cyanoacetamide in the presence of a mild catalyst and a solvent at a temperature of about 50° C. to about 115° C., to provide a 3-O-alkylated entacapone of formula (4):

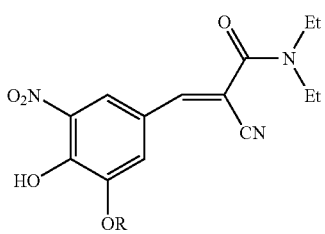

(4)

wherein R is methyl or ethyl;

(ii) treating the 3-O-alkylated entacapone with an acid catalyst in the presence of an organic base and one or more solvents at a temperature of about 20° C. to about 60° C., to provide the crude compound of formula I; and (iii) optionally purifying the crude compound of formula I using a solvent or a mixture of solvents to provide a purified entacapone.

The solvent in step (i) can be an organic solvent, for example a protic solvent (e.g., an alcohol) or an aryl solvent, such as a ($C_1$-$C_6$)alcohol, a ($C_1$-$C_5$)alcohol (e.g., methanol or ethanol), benzene, toluene, xylene, or a combination thereof.

Step (i) can be carried out in the presence of pyridine or a piperidine salt such as piperidine acetate and piperidine propionate, pyridinium acetate and pyridium propionate and pyridinium para-toluenesulfonate etc. In another embodiment, step (i) can be carried out in the presence of pyridine, piperidine, a pyridinium salt, a piperidine salt, or a combination thereof. The counter ions of the salts can be any organic cation, such as acetate, propionate, or para-toluenesulfonate.

The reaction temperature in step (i) can be about 60° C. to about 115° C., preferably about 75° C. to about 110° C., and more preferably about 100° C. to about 110° C. The solvent in step (i) can be isopropyl alcohol, ethanol, n-butanol, toluene, or a combination thereof. The reaction time for the condensation of the 3-alkoxy-4-hydroxy-5-nitrobenzadehyde and N,N-diethylaminocyanoacetamide can be about 15 hours to about 25 hours. The mild catalyst can be an acid, for example, acetic acid.

The reaction temperature for step (ii) can be about 25° C. to about 50° C. The solvent used in step (ii) can be an organic solvent, such as a chlorinated solvent, an ether solvent, or a combination thereof. A chlorinated solvent can be used in step (ii) alone or in combination with other chlorinated solvents, in combination with an ethereal solvent (such at THF), or both. In one embodiment, the chlorinated solvent can be one or more of chloroform, methylene dichloride, and ethylene dichloride.

The solvent used for purification in step (iii) can be an aryl solvent or an alcohol. Typical examples of such solvents include toluene, isopropyl alcohol, methanol, toluene, and combinations thereof.

The invention also provides a compound of formula (4):

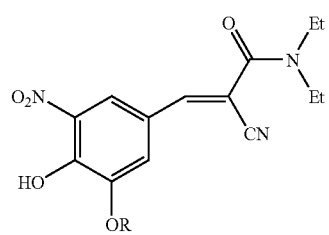

(4)

wherein R is ethyl. R can also be methyl. The double bond of the compound of formula (4) can be in the E-orientation, or in the Z-orientation.

The invention further provides a method for preparing a compound of formula (4):

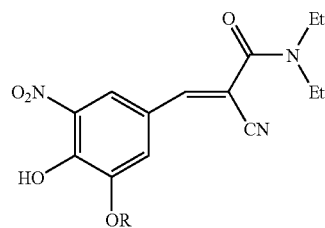

(4)

wherein R is methyl or ethyl, comprising contacting a compound of formula (2):

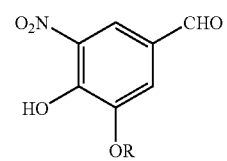

(2)

where R is methyl or ethyl, with N,N-diethylaminocyanoacetamide in the presence of a mild catalyst and a solvent at a temperature of about 50° C. to about 115° C., to provide the compound of formula (4). Further details of the procedure for preparing the compound of formula (4) are described above, and in the Detailed Description below.

DETAILED DESCRIPTION OF THE INVENTION

An objective of the present invention is to provide an improved process for the preparation of Entacapone.

Another objective of the present invention is to provide an improved process for the preparation of Entacapone using a 3-alkoxy-4-hydroxy-5-nitrobenzadehyde of formula (2) (a guaiacol derivative). A further objective of the invention is to provide a compound of formula (4) where R is methyl or ethyl, which is also a guaiacol derivative, and is stable at room temperature. Compound 4 does not change color during two months storage.

Yet another objective of the present invention is to provide an improved process for the preparation of Entacapone by reducing the reaction time and making the reaction go to completion, thereby making the process economical.

Still another objective of the present invention is to provide an improved process for the preparation of Entacapone by avoiding the use of 3,4-dihydroxy-5-nitrobenzaldehyde.

Yet another objective of the present invention is to provide an improved process for the preparation of Entacapone employing intermediates, such as a compound of formula 4, where R is methyl or ethyl.

Another objective of the present invention is to provide a novel intermediate, such as a compound of formula 4 where R is ethyl.

Still another objective of the present invention is to provide a process for the preparation of a novel intermediate of the formula 4 where R is methyl or ethyl.

The compound of the formula 4 wherein R is methyl is known as metabolite in Entacapone (Drug Metabolism and Disposition (1993), 21, 81-92) but has hitherto been prepared by any chemical method. Furthermore, the compounds of the formula 4 where R is methyl or ethyl have not been hitherto known as intermediates for the preparation of Entacapone.

To achieve the above objectives, an entirely different strategy was devised for the preparation of Entacapone.

Accordingly, the process envisaged and developed involves the reaction shown in the Scheme 2.

Scheme 2.

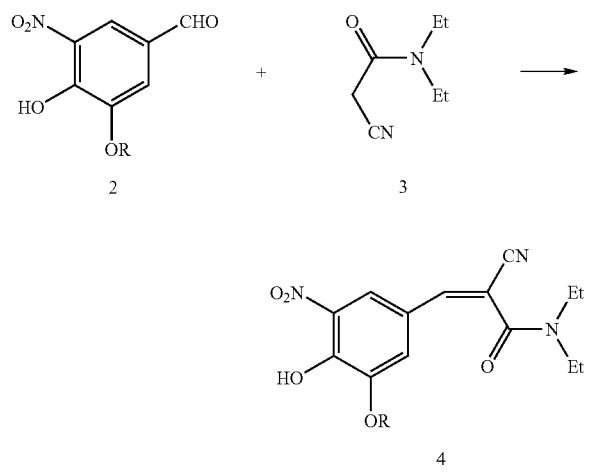

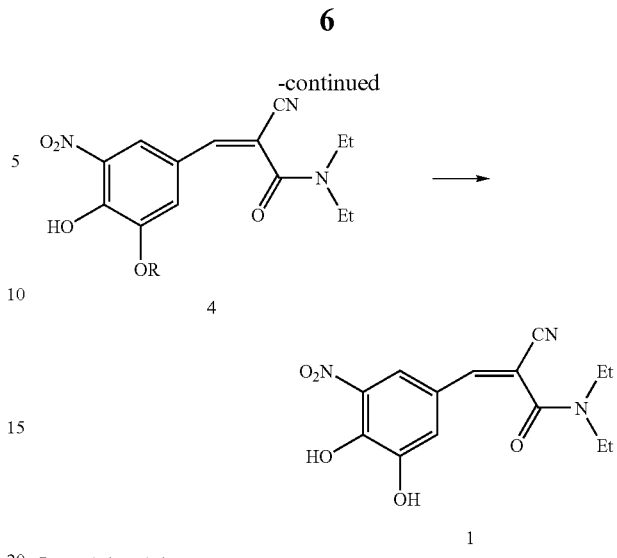

R = methyl or ethyl.

Accordingly, in one embodiment the present invention provides an improved process for the preparation of Entacapone which comprises:

(i) reacting a 3-alkoxy-4-hydroxy-5-nitrobenzadehyde of formula (2) with N,N-diethylaminocyanoactamide of formula (3) in the presence of a mild acid catalyst and a solvent at a temperature in the range of about 50-115° C., to provide an intermediate of formula (4) wherein R is methyl or ethyl;

(ii) treating the 3-O-alkylated (methyl or ethyl) Entacapone of the formula (4) with acid catalysts in the presence of an organic base and solvents at a temperature in the range of about 20-60° C. to provide crude Entacapone; and (iii) optionally purifying the crude entacapone obtained in step (ii) by using solvent or a mixture thereof (i.e., a combination of solvents).

In a preferred embodiment of the invention, step (i) may be carried out using solvents such as $(C_1-C_5)$alcohols or toluene in presence of pyridine and piperidine salts such as piperidinium acetate, piperidinium propionate and pyridinium para-toluenesulfonate, etc. The reaction temperature used in this step can be preferably between 70-115° C., and more preferably between 110 to 115° C. The solvent can be selected from, for example, isopropyl alcohol, ethanol, n-butanol, toluene, etc., and combinations thereof.

It was observed that the intermediate of formula 4 where R is methyl or ethyl exists in two isomeric forms. Although the isomer where R is methyl could be separated, despite repeated and best efforts, the isomers of the compound where R is ethyl proved inseparable. However, the non-separation of the isomers does not affect the conversion of the compound of formula 4 where R is methyl or ethyl for its conversion to Entacapone.

Another significant aspect of this invention is that on formula (4) where R is methyl or ethyl, the cyano group is very susceptible to hydrolysis. Even at mild acidic and basic condition it can convert to the corresponding amide or acid and subsequently the compound to revert back to the starting material (formula (2)). However, by careful design and execution of the dealkylation, Entacapone can be obtained in good yield by conducting the reaction at, for example, about room temperature or between about 25° C. and about 50° C.

Another aspect of this invention is that the reaction time for condensation of the formula (2) and formula (3) is only about 17 hours and the reaction goes to completion, thereby increasing the yield to about 86%. The overall yield from compound of the formula (2) over two stages is about 80%.

Yet another important aspect of this invention is that the intermediate of formula (4) where R is methyl or ethyl is stable and there is no color change under normal storage conditions.

The another aspect of this invention is that the dealkylation, which normally required higher temperature, is presently carried out at about 25-50° C. The solvents which can be employed include chloroform, methylene dichloride, ethylene dichloride, tetrahydrofuran, etc., and combinations thereof.

The solvents that can be employed in purification of the crude Entacapone may be aromatic or alcoholic solvents, such as toluene, isopropyl alcohol, methanol, acetone, or mixtures thereof.

The details of the process of this invention are described in the Examples given below, which are provided only by way of illustration and therefore should not be construed to limit the scope of the invention.

EXAMPLES

Example 1

STEP 1: Preparation of N,N-diethyl-2-cyano-3-(3-ethoxy-4-hydroxy-5-nitrophenyl)acrylamide (Formula 4; R=ethyl).

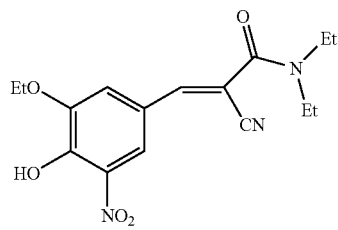

A flask was charged with 3-ethoxy-4-hydroxy-5-nitrobenzaldehyde (20 g, 0.0947 mole) (formula 2 where R is ethyl) and N,N-diethylaminocyanoacetamide (formula (3)) (14.6 g, 0.1042 mol), acetic acid (3.13 g), and piperidine (4.45 g), along with toluene (200 mL), and was heated to a reflux temperature of about 100-115° C. with continuous removal of water azeotrophically for about 15 hours. After the reaction was complete, the reaction mixture was concentrated to a volume of 20-30 mL, quenched into dilute hydrochloric acid and chilled water (200 mL), and stirred for 60 minutes. The precipitated solid was filtered and dried to provide 30 g (95% yield, HPLC purity of 94% (including isomer)) of N,N-diethyl-2-cyano-3-(-3-ethoxy-4-hydroxy-5-nitrophenyl)acrylamide. The product was used as such directly to the next stage. MR=110.0-117.2° C.

STEP 2: Preparation of N,N-diethyl-2-cyano-3-(3,4-dihydroxy-5-nitrophenyl) acrylamide (Entacapone).

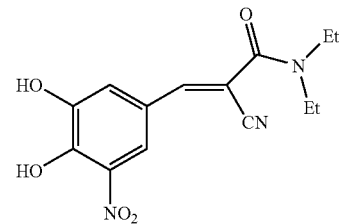

N,N-Diethyl-2-cyano-3-(3-ethoxy-4-hydroxy-nitrophenyl)acrylamide (5 g, 0.0150 mole) (formula 4 where R is ethyl), obtained by the process described in step (i) above was charged with pyridine (12.5 mL) along with dichloromethane (50 mL), stirred and cooled to 0-5° C. degrees, slowly charged the aluminum chloride (10 g, 0.751 mol) while keeping the temperature below 5° C., and stirred at 0-5° C. for 30 minutes. After maintaining for 30 minutes, the reaction mixture was slowly raised to 40-45° C. and stirred at that temperature for 50 hours. After reaction completion, the solvent was removed to provide a residual volume of 10 mL, the residual volume was quenched into dilute hydrochloric acid and chilled water (50 mL), and stirred for 30 minutes. The formed product was filtered and dried. The dried weight was 4 g (87.3% yield, HPLC purity of about 93.25%). The crude material was purified using methanol and toluene as a solvent system to provide Entacapone as a pure product, having HPLC purity of 99.5% and an IR spectrum that matched the reported spectrum. MR=162-163° C.; HPLC=99.76%; PMR=200 MHz (DMSO-d6); δ value; 1.26 (m, 6H), 3.49(q, 4H), 7.50(s, 1H,), 7.905 (d, 1H,J=0.01), 7.99(1H, J=0.01). MS=M/Z=306.4 (M+1).

Example 2

STEP 1: Preparation of N,N-diethyl-2-cyano-3-(3-methoxy-4-hydroxy-5-nitrophenyl) acrylamide (Formula 4; R=methyl).

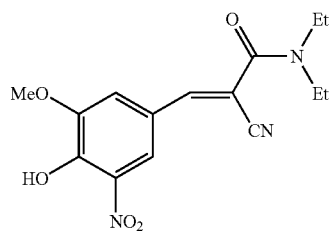

A flask was charged with 3-methoxy-4-hydroxy-5-nitrobenzaldehyde (25 g, 0.126 mole) (formula 2 where R is methyl) and N,N-diethylaminocyanoacetamide (formula (3)) (22.2 g, 0.158 mole), acetic acid (4.18 g) and piperidine (5.94 g), along with toluene (250 mL) and was heated to a reflux temperature of about 105-110° C. Water was removed azeotrophically for 15 hours. The reaction mixture was concentrated and quenched into dilute hydrochloric acid and chilled water (375 mL), and stirred for 3 hours. The precipitated solid was filtered and dried to provide 36 g (88.95% yield, HPLC purity of 94.2% (including isomer)) of the N,N-diethyl-2-cyano-3-(3-methoxy-4-hydroxy-5-nitrophenyl)acrylamide, which was used as such for the next stage.

A small sample was purified to get the pure single isomer (HPLC) by crystallizing from methanol. The pure product had the following properties: HPLC PURITY: 99.63%; MR: 130-132° C.; IR (cm$^{-1}$): 2204 (—CN), 1637 (—C=O); PMR (200 MHz), δvalue; 1.28 (m, 6H), 3.49 (q, 4H), 4.02 (s, 3H), 7.608 (s, 1H), 8.02 (d, 1H, J=0.01), 7.98 (s, 1H, J=0.01); MS: M/Z=320.2 (M$^{+1}$).

STEP 2: Preparation of N,N-diethyl-2-cyano-3-(3,4-dihydroxy-5-nitrophenyl) acrylamide (Entacapone):

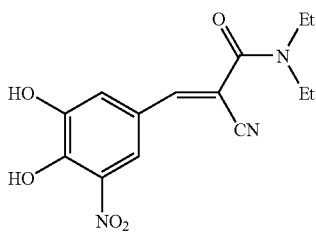

N,N-Diethyl-2-cyano-3-(3-methoxy-4-hydroxy-5-nitrophenyl)acrylamide (20 g, 0.062 mole) (formula 4 where R is methyl), obtained by the process described in step(i) of Example 2 above, was charged with pyridine (50 mL) along with dichloromethane (120 mL), was stirred and cooled to 0-5° C., slowly charged with aluminum chloride (32 g, 0.239 mole) while keeping the temperature below 5° C., and was stirred at 0-5° C. for 30 minutes. After maintaining for 30 minutes, the reaction mixture temperature was slowly raised to room temperature, and then to 40-45° C. and stirred for 2 hours. The reaction mixture was quenched in dilute hydrochloric acid and ice water (50 mL) after removing the methylene chloride, and was stirred for 60 minutes. The formed product was filtered and dried. The dried weight was 18 g (94.1%) with HPLC purity of about 94.42%.

The crude product was purified using methanol and toluene as a solvent to provide the Entacapone as a pure product having HPLC purity of 99.5%. Its spectra matched that of the product obtained from Example 1 (step 2).

As can be seen by the results of the Examples, various advantages of the invention include: the process is simple and economical; the reaction time necessary to prepare Entacapone has been reduced compared to known methods, and the reaction sequence described herein goes to completion, where currently known methods do not. The process avoids the use of 3,4-dihydroxy-5-nitrobenzaldehyde. The process also results in a new intermediate: formula 4 where R is ethyl.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing a compound of formula I:

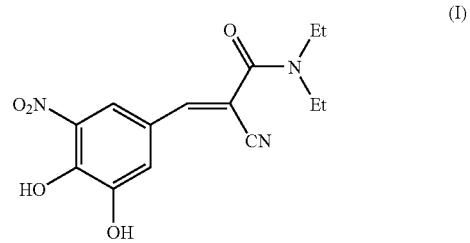

comprising:
(i) contacting a 3-alkoxy-4-hydroxy-5-nitrobenzadehyde where the alkyl group of the alkoxy is a methyl or an ethyl group, with N,N-diethylamino-cyanoacetamide in the presence of a mild acid catalyst and a solvent at a temperature of about 50° C. to about 115° C., to provide a 3-O-alkylated entacapone of formula (4):

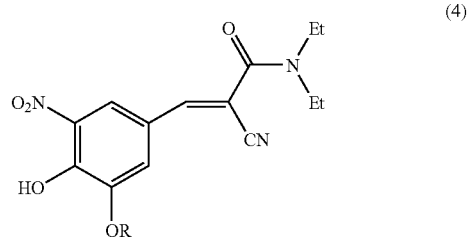

wherein R is methyl or ethyl;
(ii) treating the 3-O-alkylated entacapone with an acid catalyst in the presence of an organic base and one or more solvents at a temperature of about 20° C. to about 60° C., to provide the crude compound of formula I; and
(iii) optionally purifying the compound of formula I using a solvent or a mixture of solvents to provide a purified entacapone.

2. The method of claim 1 wherein the solvent in step (i) is a (C$_1$-C$_5$)alcohol, toluene, or a combination thereof.

3. The method of claim 1 wherein step (i) is carried out in the presence of pyridine, piperidine, a pyridinium salt, a piperidine salt, or a combination thereof.

4. The method of claim 1 wherein the reaction temperature in step (i) is about 60 degrees C to about 115 degrees C.

5. The method of claim 1 wherein the solvent in step (i) is isopropyl alcohol, ethanol, n-butanol, toluene, or a combination thereof.

6. The method of claim 1 wherein the reaction time for the condensation of the 3-alkoxy-4-hydroxy-5-nitrobenzadehyde and N,N-diethylaminocyanoacetamide is about 15 hours to about 25 hours.

7. The method of claim 1 wherein the reaction temperature for step (ii) is about 25 degrees C to about 50 degrees C.

8. The method of claim 1 wherein a chlorinated solvent is used in step (ii).

9. The method of claim 8 wherein the chlorinated solvent is chloroform, methylene dichloride, ethylene dichloride, or a combination thereof.

10. The method of claim 1 wherein the solvent used for purification in step (iii) is toluene, isopropyl alcohol, methanol, toluene, or a combination thereof.

11. A method for preparing a compound of formula (4):

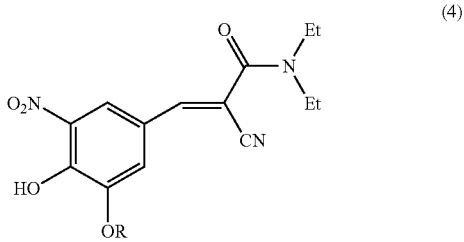

(4)

wherein R is methyl or ethyl, comprising contacting a compound of formula (2):

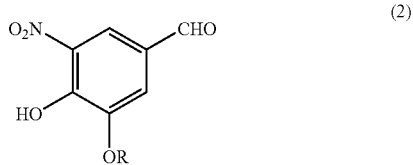

(2)

where R is methyl or ethyl, with N,N-diethylaminocyanoacetamide in the presence of a mild catalyst and a solvent at a temperature of about 50 degrees C to about 115 degrees C, to provide the compound of formula (4).

12. The method of claim 11 wherein the solvent is a ($C_1$-$C_5$)alcohol, toluene, or a combination thereof.

13. The method of claim 11 wherein the contacting of the compound of formula (2) and N,N-diethylaminocyanoactamide is carried out in the presence of pyridine, piperidine, a pyridinium salt, a piperidine salt, or a combination thereof.

14. The method of claim 11 wherein the reaction temperature is about 60 degrees C to about 115 degrees C.

15. The method of claim 11 wherein the reaction temperature is about 75 degrees C to about 110 degrees C.

16. The method of claim 11 wherein the solvent is a protic solvent, toluene, or a combination thereof.

17. The method of claim 11 wherein the mild catalyst is an acid.

18. The method of claim 16 wherein the acid is acetic acid.

19. The method of claim 11 wherein the solvent comprises toluene.

\* \* \* \* \*